(12) United States Patent
Takahashi

(10) Patent No.: US 6,761,321 B2
(45) Date of Patent: Jul. 13, 2004

(54) THERMOSTAT DEVICE

(75) Inventor: Masanori Takahashi, Tokyo (JP)

(73) Assignee: Nippon Thermostat Co., Ltd., Kiyose (JP)

( * ) Notice: Subject to any disclaimer, the term of this patent is extended or adjusted under 35 U.S.C. 154(b) by 0 days.

(21) Appl. No.: 10/311,209

(22) PCT Filed: Apr. 8, 2002

(86) PCT No.: PCT/JP02/03516

§ 371 (c)(1),
(2), (4) Date: Dec. 16, 2002

(87) PCT Pub. No.: WO02/090737

PCT Pub. Date: Nov. 14, 2002

(65) Prior Publication Data

US 2003/0183701 A1 Oct. 2, 2003

(30) Foreign Application Priority Data

Apr. 27, 2001 (JP) ........................................ 2001-130920

(51) Int. Cl.$^7$ ................................................ F01P 7/12
(52) U.S. Cl. .................................... 236/34.5; 236/68 R
(58) Field of Search ...................... 236/34, 34.5, 68 R; 123/41.09; 165/299

(56) References Cited

U.S. PATENT DOCUMENTS

| | | | | |
|---|---|---|---|---|
| 4,370,950 A | * | 2/1983 | Furukubo | 123/41.08 |
| 4,560,104 A | * | 12/1985 | Nagumo et al. | 236/34.5 |
| 4,606,302 A | * | 8/1986 | Huemer et al. | 236/34.5 |
| 4,621,594 A | * | 11/1986 | Kubis | 123/41.09 |
| 4,976,462 A | * | 12/1990 | Hirata et al. | 236/34.5 |
| 5,238,185 A | * | 8/1993 | Saur et al. | 236/34.5 |
| 5,385,296 A | * | 1/1995 | Kurz et al. | 236/34.5 |

FOREIGN PATENT DOCUMENTS

| | | |
|---|---|---|
| FR | 2729715 | 7/1996 |
| JP | 83224/1982 | 5/1982 |
| JP | 10-220633 | 8/1998 |

* cited by examiner

Primary Examiner—William E. Tapolcai
(74) Attorney, Agent, or Firm—Oblon, Spivak, McClelland, Maier & Neustadt, P.C.

(57) ABSTRACT

An object of the present invention is to provide a thermostat device which enables a valve body to operate with stability, which can prevent overshoot and hunting, and in which the size of the thermostat device itself can be reduced. A first valve body and a second valve body are removably supported on a main shaft which is supported by the distal end of a piston of a thermo-element which causes the first valve body and second valve body to open and close by sensing the temperature of cooling water, and a temperature sensing section of said thermo-element is disposed so as to sense cooling water temperature by contacting only the cooling water from the engine outlet side without directly contacting the cooling water from the radiator outlet side. A heat-generating element is attached to the temperature sensing section, and thus in addition to the opening and closing of the first valve body and second valve body by the thermo-element in accordance with the temperature of the cooling water, [the opening and closing of the first and second valve bodies are freely controlled by the application of a current to the heat-generating element$^{vi}$]. The device is constituted such that a third influx sleeve is disposed below the second valve body, the first valve body is disposed above the second valve body, the thermo-element is disposed above the first valve body, and the first influx sleeve is provided between the thermo-element and the main valve.

4 Claims, 5 Drawing Sheets

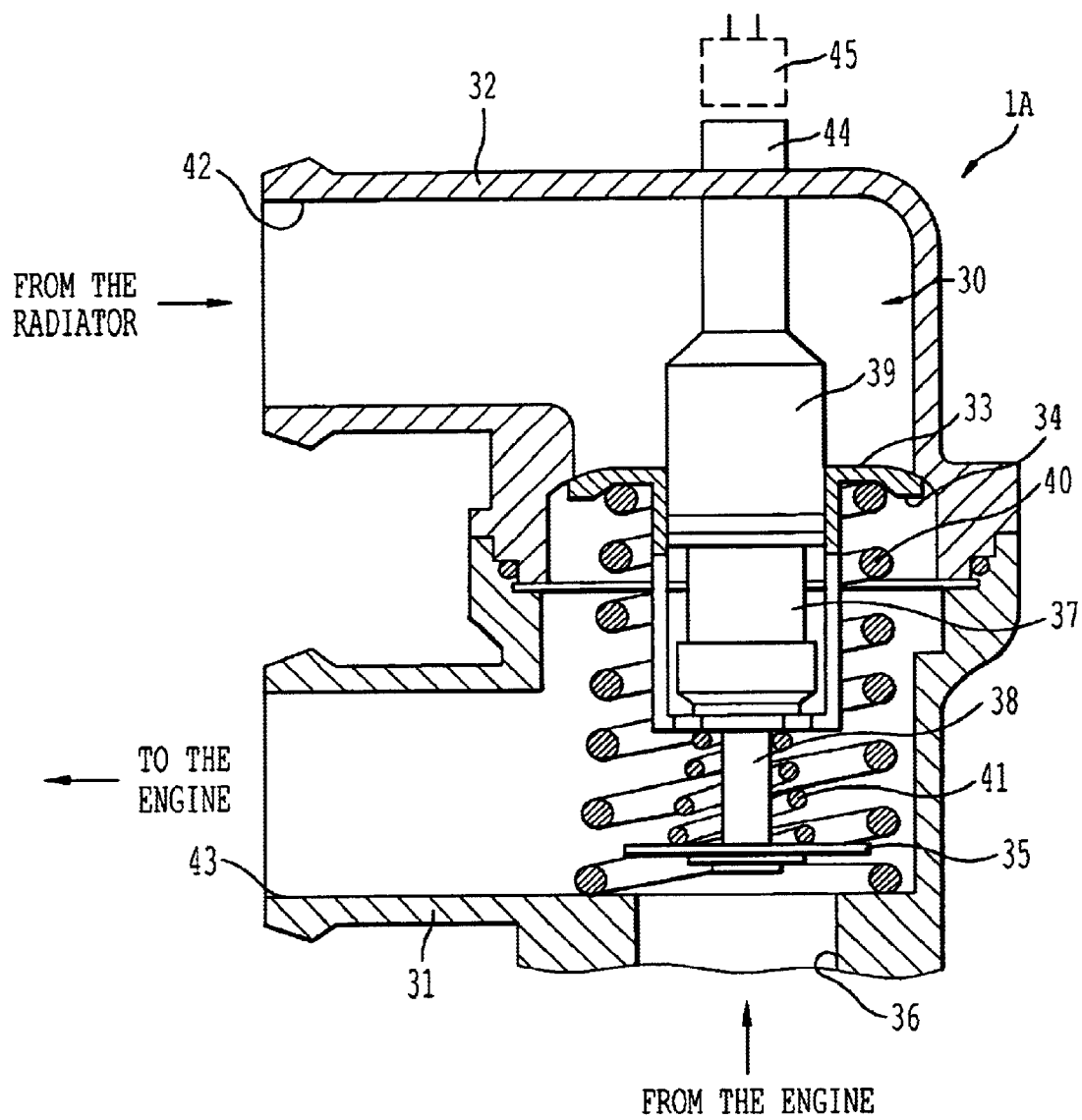

THERMOSTAT DEVICE

TECHNICAL FIELD

This invention relates to a thermostat device which is responsible for cooling an internal combustion engine, and more particularly to a thermostat device which has lower flow resistance than a conventional thermostat, which can control the operation of a valve body regardless of the cooling water temperature at the time of engine start-up, and which can achieve early warming of the engine, an improvement in fuel economy, and the prevention of overheating by being able to control the flow rate of the cooling water which circulates through a heating circuit or the like.

BACKGROUND ART

Thermostat devices disposed in the cooling systems of internal combustion engines and the like comprise a sensor case having an in-built thermal expansion body which perceives temperature changes in cooling water which fills the circulation channels of a cooling system and expands and contracts accordingly. The valve body opens and closes in response to volumetric change accompanying the expansion and contraction of the thermal expansion body, and thus the thermostat device functions to maintain cooling liquid at a predetermined temperature.

An example of a conventional thermostat device is illustrated in FIG. 7. This thermostat device 1A comprises a thermostat operating section 30 which serves as the driving section of the valve bodies inside valve housing 31, 32, which is constituted by two members. The thermostat operating section 30 is fixedly supported by the valve housing 32, and a first valve body 33 and a second valve body 35 (bypass valve) are operated by an operating piston 9 which is built into the thermostat operating section 30, whereby a main channel 34 and a bypass channel 36 are controlled.

The housing 37 of the thermostat operating section 30 is supported by a holder 39, and this holder 39 surrounds the end of the housing 37 on the side at which the piston protrudes and the end of the opposite side in cap-form. The cap-form holder 39 is supported by the valve housing 32.

A central region with a pot-shaped cross section is provided in the first valve body 33, and the thermostat operating section 30 is disposed in this central portion. When the first valve body 33 is in a closed position, this central region, together with the holder 39, blocks the main channel 34.

A bolt 38 is provided as an extension in the axial direction of the operating piston (not shown) of the thermostat operating section 30. A second valve body 35 (bypass valve) is attached to this bolt 38 by a sliding guide and opens and closes a bypass channel 36. The second valve body 35 (bypass valve) is biased by a spring member 41. The first valve body 33 is biased by a spring member 40, and this spring member 40 is supported by the valve housing 31.

The thermostat device 1A constituted in this manner is disposed such that when cooling water from the engine$^i$ enters from the sleeve 42, this cooling water circulates from the bypass channel 36 to the engine or through the sleeve 43 to the radiator$^i$. Directly after engine start-up, the cooling water is at a low temperature, and therefore the cooling water which enters from the bypass 36 is returned directly to the engine. When the cooling water reaches a predetermined temperature following the completion of engine warm-up, wax inside the housing 37 senses this temperature and expands accordingly, thereby causing the operating piston (not shown) of the thermostat operating section 30 to expand. As a result of the expansion of the operating piston, the first valve body 33 falls against the urging force of the spring member 40, thereby switching the main channel 34 from a blocked state to an open state, and the second valve body 35 (bypass valve) blocks the bypass channel 36. As a result, the cooling water from the sleeve 42 passes through the sleeve 43 and flows into the engine.

In order to force the wax inside the housing 37 to expand, a heating part 44 is provided in the housing 37, and this heating part 44 is caused to protrude from the valve housing 32 and connect to a superheater element 45.

In such a conventional thermostat device 1A, however, the housing 37 which serves as the cooling water temperature sensing portion is disposed inside the cooling liquid channels, and hence flow resistance in the cooling water entering from the sleeve 42 is large. It is therefore difficult to miniaturize the water pump which forces the cooling water to circulate.

Furthermore, during engine warm-up directly after engine start-up, the cooling water from the engine and the cooling water from the radiator become mixed in the vicinity of the housing 37, which may produce a hunting phenomenon. When such a phenomenon is produced, the temperature of the cooling water which flows into the engine becomes unstable, making it difficult to improve fuel economy and achieve early warming. As a preventative measure, it has been necessary to adjust the structure of the valve housing 32 or to attach a current plate, also known as a baffle plate, directly before the housing 37 which serves as, the temperature sensing portion in order to mix the cooling water.

Moreover, when the thermostat device 1A is disposed for inlet control, cooling water entering from the radiator is sometimes perceived, and as a result, malfunctions such as overheating may occur. Also, with the aim of compressing engine warm-up time, some devices are constituted such that the bypass valve body is closed and the flow rate of the cooling water flowing through the bypass channel is reduced to a minimum or halted completely, even when the temperature of the cooling water is low prior to engine warm-up, in order to avoid heat radiation from the bypass channel or from a heater radiator for heating the vehicle interior or various devices for controlling the engine provided at points in the bypass channel. However, since the flow of cooling water virtually ceases, heat spots may occur in the interior of the engine, or breakdowns of the engine or the thermostat may occur due to the negative suction pressure on the water pump.

If a further valve body is provided separately from the main valve body and bypass valve body in order to provide separate control for a heater radiator for heating the interior of the vehicle or various device circuits for controlling the engine, or if these circuits are integrated and controlled by the bypass valve body only, then the bypass channel has to be enlarged, whereupon problems arise such as construction becoming more complicated and the size of the device increasing.

DISCLOSURE OF THE INVENTION

The thermostat device according to the present invention has been devised in consideration of these problems, and it is an object of the present invention to provide a thermostat device in which early warming of an internal combustion engine can be achieved even at engine start-up time, in which fuel consumption can be reduced, and in which flow resistance of cooling water is low.

In order to solve the aforementioned problems, the thermostat device according to the present invention has a constitution in which a first valve body and a second valve body are removably supported on a main shaft which is supported by the distal end of a piston of a thermo-element which causes the first valve body and second valve body to open and close by sensing the temperature of cooling water, a temperature sensing section of the thermo-element is disposed so as to sense cooling water temperature by contacting only the cooling water from the engine outlet side without directly contacting the cooling water from the radiator outlet side, and a heat-generating element is attached to the temperature sensing section. Thus, in addition to the opening and closing of the first valve body and second valve body by the thermo-element in accordance with the temperature of the cooling water, the opening and closing of the first and second valve bodies are freely controlled by the application of a current to the heat-generating element.

According to such a constitution, a temperature hunting phenomenon in the cooling water temperature, which is produced when cooling water cooled to a low temperature in the radiator flows into the device all at once immediately after the opening of the first valve body, can be prevented, and an improvement in fuel economy and rapid heating[ii] of the cooling water can be achieved. Thus, since the cooling water is mixed directly before the housing which serves as the temperature sensing portion, there is no need for any structural improvements to the valve housing or to install a current plate.

The device also has a constitution comprising: upper housing in which a first influx sleeve through which cooling water enters from the engine outlet and a second influx sleeve through which cooling water enters from the radiator are disposed so that the cooling water in each of the sleeves does not mix, and in which the first valve body is disposed such that the thermo-element opens and closes the second sleeve through which cooling water enters from the radiator by sensing the temperature of the cooling water from the first influx sleeve; and lower housing in which a mixing chamber is formed for mixing the cooling water from the engine outlet, or the cooling water from the engine outlet and the cooling water from the radiator, and a main channel is formed for emitting the cooling water from the mixing chamber to the engine.[iii]

By respectively forming the channel and the mixing chamber in the interior of the housing in this manner, the interior structure of the thermostat device can be simplified, the housing itself can be constructed integrally from a resinous material such as heat-resistant plastic, and thus the thermostat device can be made responsive to unitization.

The device also has a constitution in which a third influx sleeve is formed in the lower housing so that the cooling water from a heater for heating the interior of a vehicle and cooling water which circulates through various internal combustion engine control devices can be controlled to flow into the mixing chamber by means of the opening and closing of the second valve body.

According to such a constitution, the flow rate in the bypass channel can be reduced without reducing or halting the flow rate in the heater circuit or various device circuits, and as a result early warming of the engine becomes possible.

Furthermore, the heater circuit and various device circuits can be provided completely independently of the bypass channel, and therefore, for example, the influx inlet for cooling water from the engine outlet can be directly attached to the cooling water outlet of the engine[iv].

It is also possible to improve the cooling efficiency of the engine when the temperature of the cooling water is high by using the second valve body to reduce or halt the flow rate in the heater circuit and various device circuits, thereby relatively increasing the radiator flow rate. Early warming of the engine, an improvement in fuel economy, and prevention of overheating may also be achieved.

Further, the device has a constitution in which the third influx sleeve is disposed below the second valve body, the first valve body is disposed above the second valve body, the thermo-element is disposed above the first valve body, and the first influx sleeve is provided between the thermo-element and the main valve.

According to such a constitution, there is no need to dispose the thermo-element inside the cooling water channel inside the housing, and thus flow resistance in the cooling water can be reduced and the structure of the thermostat device can be simplified and reduced in size. Furthermore, by varying the flow rate from the first influx sleeve, or in other words altering the diameter of the sleeve to alter the flow rate ratio with the other channels, the responsiveness of the thermo-element can be easily modified. The balance with the heating value of the heat-generating element can also be easily adjusted.

The device also has a constitution in which the thermo-element is disposed such that the cooling water from the first influx sleeve only comes into contact with one part of the temperature sensing portion of the thermo-element, and a heat-generating element is provided outside of the cooling water channels.

According to such a constitution, the amount of cooling water which is temperature-sensed by the thermo-element may be easily altered simply by modifying the interior structure of the housing, and thus the responsiveness of the thermo-element can be easily modified. The balance with the heating value of the heat-generating element can also be easily adjusted.

Moreover, by disposing the heat-generating element outside of the cooling water channels, electrical reliability and maintenance can be enhanced.

BRIEF DESCRIPTION OF THE DRAWINGS

FIG. 7 is a cross sectional view illustrating a conventional poppet type thermostat having a bypass structure.

BEST MODES FOR CARRYING OUT THE INVENTION

Embodiments of the thermostat device according to the present invention thus constituted will be explained with reference to the attached drawings.

Figure 3:
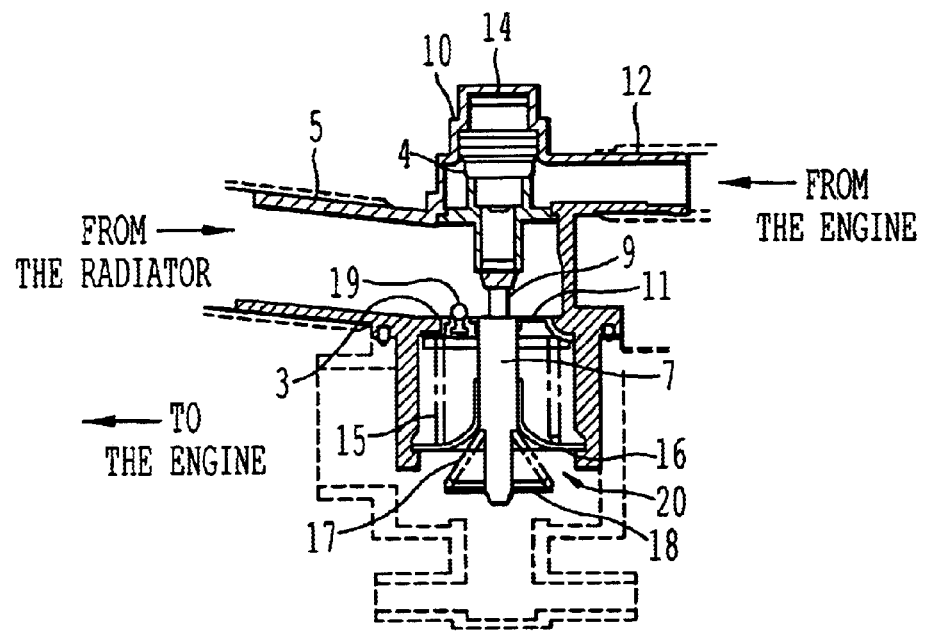
FIG. 3 is a longitudinal cross section of FIG. 2.
Figure 4:
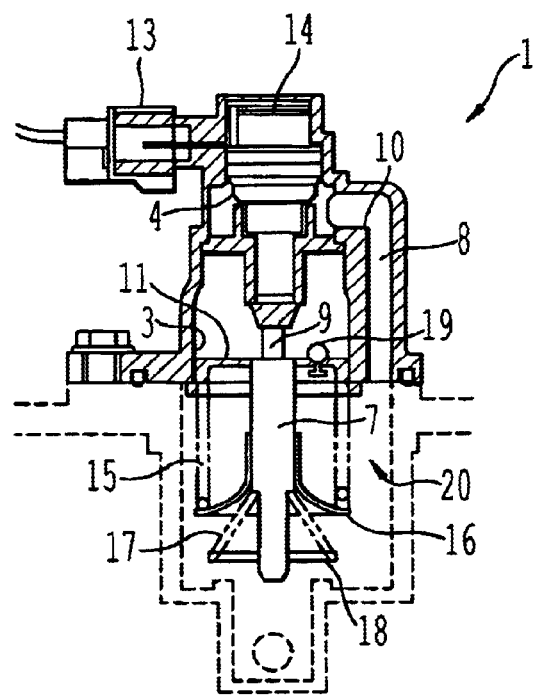
FIG. 4 is another longitudinal cross section of FIG. 2.
Figure 5:
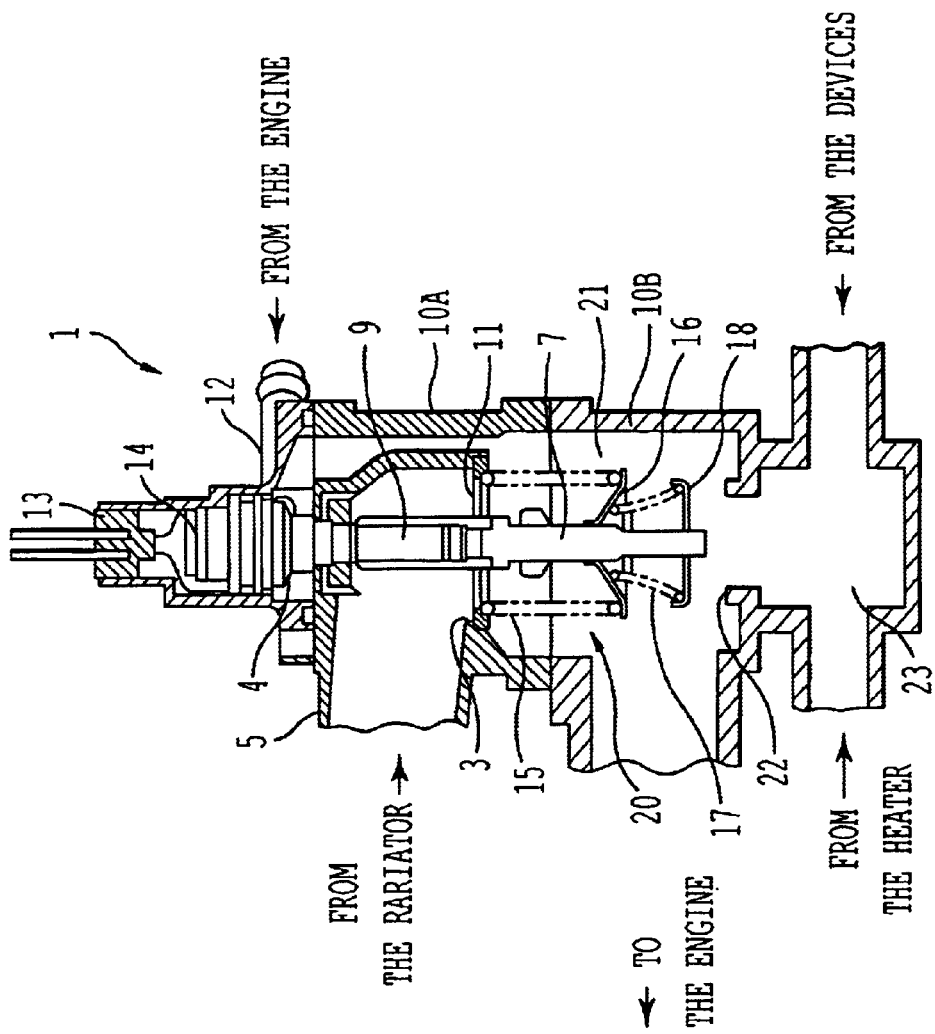
FIG. 5 is a longitudinal cross section illustrating a second embodiment of the thermostat device according to the present invention.
Figure 6:
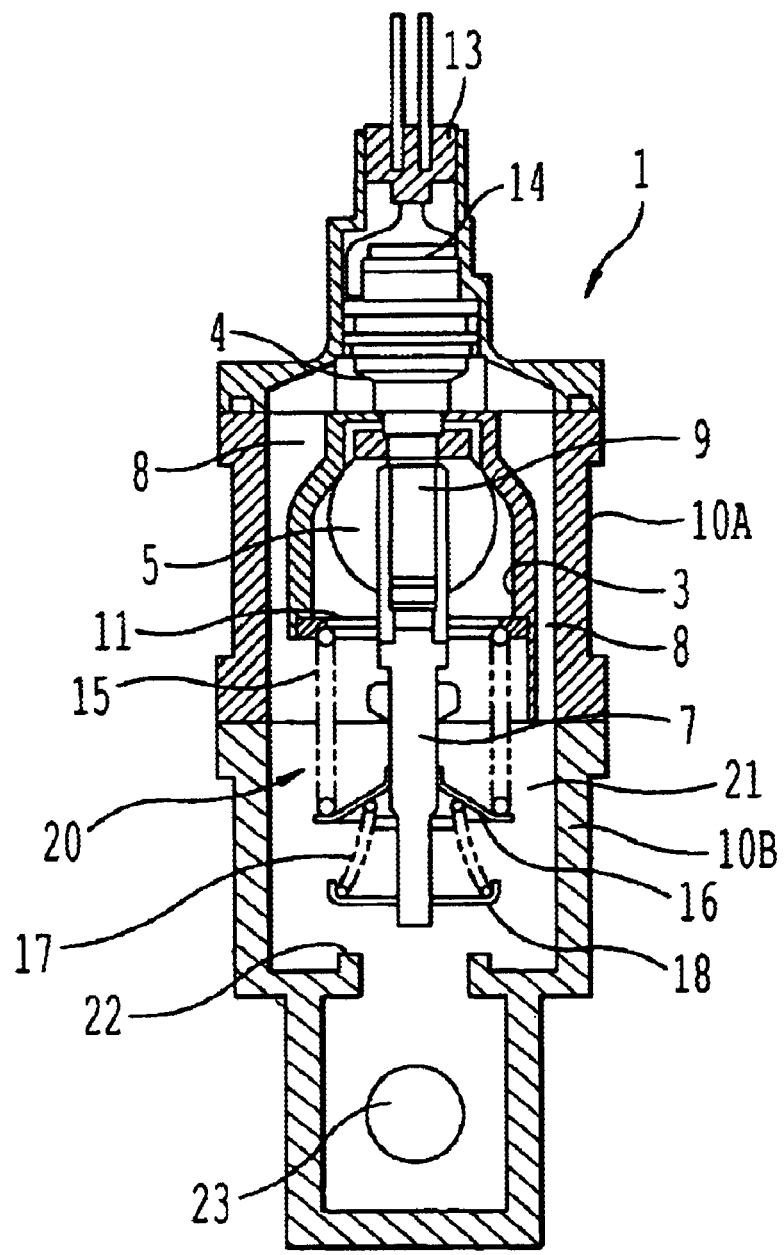
FIG. 6 is a cross sectional view illustrating the second embodiment.

FIGS. 1 through 6 illustrate embodiments of the thermostat device according to the present invention, FIGS. 1 through 4 illustrating a first embodiment, and FIGS. 5 and 6 illustrating a second embodiment.

A thermostat device 1 of the first embodiment shown in FIGS. 1 through 4 comprises a main housing body 10 which is integrally formed from a resinous material such as heat-resistant plastic, and a valve driving section 20 which opens and closes a first valve body 11 and a second valve body 18 by means of the expansion of wax (not shown) which is housed inside an element 4 and which serves as a cooling liquid temperature sensing section. The housing 10 and valve driving portion 20 will now each be described in detail.

1. Housing 10

The housing 10 of the thermostat device 1, as noted hereinabove, is injection-molded from a resinous material such as heat-resistant plastic which is capable of sufficiently withstanding the temperature of high-temperature cooling water. Depending upon the intended purpose, the housing 10 may also be manufactured from metal. In the housing 10 are formed a bypass sleeve 12 through which cooling water directly enters the thermostat device 1 at the time of engine start-up, a main sleeve 5 through which cooling water enters the thermostat device 1 from the radiator following the completion of engine warm-up, and, as is shown in FIG. 4, a sub-channel 8 through which cooling water pumped in through the bypass sleeve 12 and having come into contact with one part of the temperature sensing section of the element 4 is emitted toward the engine, and a main channel 3 through which cooling water from the radiator is emitted toward the engine.

An element housing section is also formed inside the housing 10 in an inverted U-shape so as to be capable of supporting the element 4 itself, and is set in a position such that the cooling water entering through the bypass sleeve 12 contacts only one part of the temperature sensing section of the element 4. Further, a connector connecting section 13 is formed on the outside of the housing 10 for supplying a power source to a heat-generating element 14 which forcibly heats the element 4.

2. Valve Driving Section 20

The valve driving section 20 comprises the element 4 of a mechanism which causes a piston 9 to extend by means of interior wax which expands by sensing the temperature of the cooling water, a main shaft 7 which is connected to the distal end of the piston 9, and the first valve body 11 and second valve body 18 which are removably supported on the main shaft 7.

A disc-form frame 16 is fixed between the first valve body 11 and second valve body 18 of the main shaft 7, and a main spring 15 for biasing the first valve body 11 is fixed between the frame 16 and the first valve body 11. Also, a bypass spring 17 is fixed below the frame 16 on the main shaft 7 for biasing the second valve body 18. A jiggle valve 19 is disposed in an appropriate position on the first valve body 11 so as to perform the role of removing air when cooling water is injected.

The heat-generating element 14 is attached to the top end of the element 4 in a location at which no contact is made with the cooling water. When an electrical current is applied to this heat-generating element 14, the heat-generating element 14 heats up, and thus the element 4 can be heated regardless of the temperature of the cooling water. As a result the valve driving section 20 can be controlled, and control of the engine itself is also possible in accordance with signals from an ECU (not shown) outputted in response to the operating conditions of the engine such that the valves are opened quickly when the cooling water temperature rises due to an increase in the engine load, for example, or such that the amount of lift rises above normal levels so that the engine is cooled.

The heat-generating element 4 may be a nichrome heater, a PTC element, a peltier element, or another type, and this may be selected depending on the intended use. If a peltier element is used, then the opposite effect to that described above, in other words cooling the element, becomes possible, and thus the extent to which the thermostat is controlled can be widened.

3. Action of the thermostat device 1

When the cooling water is cold, such as at engine start-up time, the cooling water emitted from the engine outlet flows into the thermostat device 1 through the bypass sleeve 12 in the housing 10 of the thermostat device 1. The cooling water which flows into the thermostat device 1 contacts the element 4 of the valve driving section 20 and then flows directly back into the engine block through the sub-channel 8, a mixing chamber 21, and then a water pump chamber (not shown).

The cooling water which is emitted from the engine outlet also flows into the radiator, and the cooling water from the radiator also flows into the interior of the thermostat device 1 through the main sleeve 5. However, the main channel 3 is blocked by the main valve body 11 which is biased by the urging force of the main spring 15, and therefore the cooling water from the radiator cannot be emitted from' the engine. As this situation continues, the cooling water which does not pass through the radiator quickly rises in temperature. When the cooling water reaches a predetermined temperature, the temperature of this cooling water is sensed by the wax in the element 4, whereupon the wax gradually expands. As the wax expands, the piston 9 extends and the main shaft 7 which is connected via the piston 9 also extends. As the main shaft 7 extends, the first valve body 11 which is supported on the main shaft 7 falls against the urging force of the main spring 15. Thus the main channel 3 which was in a blocked state opens and the cooling water from the radiator is emitted from' the engine.

This cooling water is then mixed with the cooling water which flowed into the thermostat device 1 through the bypass sleeve 12 which serves as the engine outlet, whereupon the temperature of the cooling water is controlled and the cooling water flows directly back into the engine block via the water pump chamber.

As the temperature of the cooling water which flows into the thermostat device 1 through the bypass sleeve 12 which serves as the engine outlet rises, the wax expands further, and accordingly the degree of opening of the first valve body 11 increases. Thus the amount of low-temperature cooling water cooled in the radiator increases, whereby the temperature of the cooling water flowing into the engine block decreases and the engine is cooled.

Note that one part of the cooling water which flows through the bypass sleeve 12 from the engine is allowed to enter as is for the temperature sensing purposes of the thermo-element.

FIGS. 5 and 6 illustrate a second embodiment of the thermostat device 1. The valve driving section 20 of this thermostat device 1 has the same constitution as that of the thermostat device 1 explained in the first embodiment, and only the housing 10 differs in constitution from the thermostat device 1 of the first embodiment, having a lower housing 10B which is attached to an upper housing 10A. By constituting the housing in this manner, the thermostat device and the housing in which the channels are formed can be constructed as an integral module, thereby simplifying installment into engines of various types regardless of the engine structure. This thermostat device 1 also comprises a channel which is provided below the second valve body separately from and parallel to the bypass circuit for cooling water from a heater/device sleeve 23 which serves as a heating circuit and various device circuits. When [the temperature of] the cooling water is low such as at engine start-up time, the cooling water from the engine outlet flows into the thermostat device 1 through the bypass sleeve 12 in the housing 10 of the thermostat device 1. The cooling water inside the thermostat device 1 contacts the element 4 of the valve driving section 20 and then flows directly back into the engine block via the sub-channel 8, the mixing chamber 21, and then the water pump chamber (not shown).

At this time the wax contracts, and therefore the piston 9 retracts and the main shaft 7 which is connected via the piston 9 rises (in the upward direction in the drawing). As the main shaft 7 rises, the second valve body 18 which is supported on the main shaft 7 also rises, thereby opening the channel for cooling water which passes from the heater/device sleeve 23 to the heater circuit and various device circuits, and thus allowing the cooling water to circulate. If the engine runs under continuous heavy load conditions, for example, or if for some reason the interior of the engine overheats, the temperature of the cooling water becomes higher than normal and the wax expands further than usual. As a result, the piston 9 extends even further and the main shaft 7 which is connected via the piston 9 also extends. When the main shaft 7 extends, the second valve body 18 which is supported on the main shaft 7 comes to rest on a valve seat 22 so that the cooling water from the heater/device sleeve 23 cannot enter. As a result, the inflow rate from the radiator channel increases and the temperature of the cooling water drops, and thus damage to the engine and such due to overheating and the like can be forestalled.

INDUSTRIAL APPLICABILITY

According to the thermostat device 1 of the present invention as described above, flow resistance in cooling water inside the housing can be reduced by not disposing the element inside the housing. As a result, the interior structure of the thermostat device is simplified, the housing itself can be constructed integrally from a resinous material such as heat-resistant plastic, and the thermostat device can be made responsive to unitization.

The Hunting phenomenon which occurs in temperature immediately after the main valve body is opened can be prevented, and furthermore, fuel consumption can be reduced and cooling water can be warmed rapidly.

The cooling water is mixed directly before the housing, which serves as the temperature sensing section, and there is therefore no need for any structural improvements to the valve housing or to install a current plate.

The flow rate of the cooling water from the bypass can be reduced relative to a conventional cooling device, and furthermore, by circulating the cooling water continuously, the cooling water from the radiator can be mixed to control the temperature of the cooling water. Thus constitutional simplification, early warming of the engine, improved fuel economy, and prevention of overheating can all be achieved. By providing a heating element, the degree of opening of the valve can be varied in accordance with the engine load or outside temperature, and moreover, since the harness which supplies an electrical current to the heating element and the element is disposed outside of the channels, the sealing property is ensured such that the danger of electrical leaks disappears.

Figure 1:
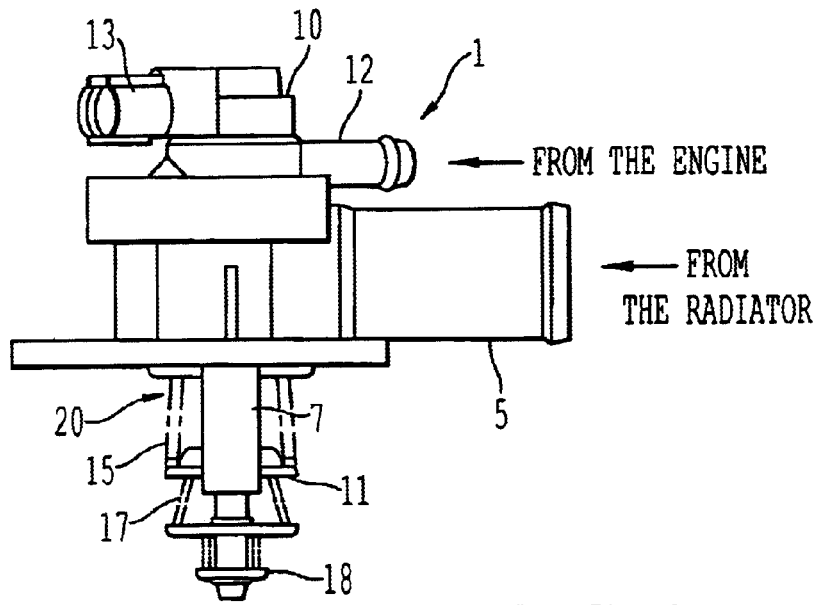
FIG. 1 is a side view illustrating a first embodiment of the thermostat device according to the present invention.
Figure 2:
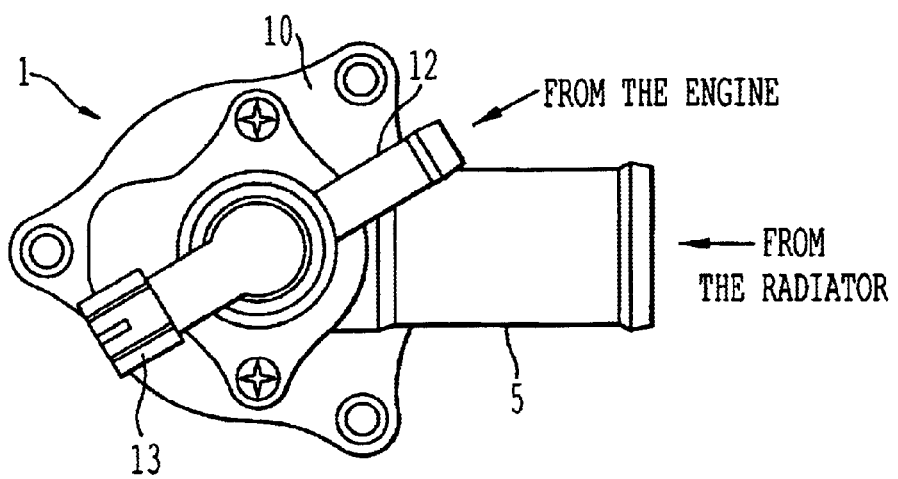
FIG. 2 is a plan view of the thermostat device of FIG. 1.

FIGS. 1 AND 2
FROM THE ENGINE
FROM THE RADIATOR
FIG. 3
FROM THE RADIATOR
FROM THE ENGINE
TO THE ENGINE
FIG. 5
FROM THE RADIATOR
FROM THE ENGINE
TO THE ENGINE
FROM THE HEATER
FROM THE DEVICES
FIG. 7
FROM THE RADIATOR
TO THE ENGINE
FROM THE ENGINE

What is claimed is:

1. A thermostat device comprising:
   a thermo-element including a temperature sensing section which is disposed so as to sense a temperature of cooling water flowing in a cooling water path by contacting the temperature sensing section only with cooling water from an engine outlet side without directly contacting cooling water from a radiator outlet side;
   a first valve body and a second valve body;
   a shaft connecting said temperature sensing section and said first and second valve bodies, said temperature sensing section being configured to move said first and second valve bodies to open and close according to the temperature of the cooling water;
   a heat-generating element attached to said temperature sensing section and configured to control movements of the first and second valve bodies to open and close;
   an upper housing including a first influx sleeve through which cooling water enters from the engine outlet and a second influx sleeve through which cooling water enters from the radiator, said first valve body being disposed in the upper housing such that said thermo-element opens and closes said second sleeve by sensing the temperature of the cooling water from said first influx sleeve; and
   a lower housing in which a mixing chamber is formed to mix the cooling water from the engine outlet, or the cooling water from the engine outlet and the cooling water from the radiator, a main channel being formed in the lower housing to discharge the cooling water from said mixing chamber to an interior of the engine,
   wherein a third influx sleeve is formed in said lower housing so that the cooling water from a heater for heating the interior of a vehicle and cooling water which circulates through various internal combustion engine control devices are controlled to flow into the mixing chamber by means of the opening and closing of said second valve body.

2. The thermostat device according to claim 1, wherein the third influx sleeve is disposed below the second valve body, the first valve body is disposed above the second valve body, the thermo-element is disposed above the first valve body, and said first influx sleeve is provided between the thermo-element and the first valve body.

3. The thermostat device according to claim 1, wherein said heat-generating element is provided outside of the cooling water path.

4. The thermostat device according to claim 2, wherein said heat-generating element is provided outside of the cooling water path.

* * * * *